United States Patent
Paolillo

(10) Patent No.: US 10,420,477 B2
(45) Date of Patent: Sep. 24, 2019

(54) PERSONAL MONITORING AND RESPONSE SYSTEM

(71) Applicant: Giancarlo Paolillo, Glen Gardner, NJ (US)

(72) Inventor: Giancarlo Paolillo, Glen Gardner, NJ (US)

(73) Assignee: Giancarlo Paolillo, Glen Gardner, NJ (US)

( * ) Notice: Subject to any disclaimer, the term of this patent is extended or adjusted under 35 U.S.C. 154(b) by 0 days.

(21) Appl. No.: 16/003,041

(22) Filed: Jun. 7, 2018

(65) Prior Publication Data
US 2019/0000333 A1    Jan. 3, 2019

Related U.S. Application Data

(60) Provisional application No. 62/528,373, filed on Jul. 3, 2017.

(51) Int. Cl.
| | |
|---|---|
| *G08B 1/08* | (2006.01) |
| *A61B 5/024* | (2006.01) |
| *A61B 5/11* | (2006.01) |
| *G16H 40/67* | (2018.01) |
| *G16H 10/60* | (2018.01) |
| *A61B 5/00* | (2006.01) |

(52) U.S. Cl.
CPC ........ *A61B 5/02438* (2013.01); *A61B 5/1112* (2013.01); *A61B 5/681* (2013.01); *A61B 5/742* (2013.01); *A61B 5/7465* (2013.01); *G16H 10/60* (2018.01); *G16H 40/67* (2018.01); *A61B 2505/07* (2013.01)

(58) Field of Classification Search
CPC .... A61B 5/02438; G06F 3/0484; H04W 4/02; G08B 25/016; G08B 25/10; G08B 21/0423; G08B 21/0225; G08B 21/04
USPC ......................................... 340/539.12, 573.1
See application file for complete search history.

(56) References Cited

U.S. PATENT DOCUMENTS

| | | | |
|---|---|---|---|
| 10,037,668 B1 * | 7/2018 | DesGarennes ..... | G08B 21/0423 |
| 2001/0044588 A1 | 11/2001 | Mault | |
| 2010/0052915 A1 * | 3/2010 | Allen ..................... | A61B 5/411 |
| | | | 340/573.1 |
| 2010/0222645 A1 | 9/2010 | Nadler | |
| 2012/0203076 A1 | 8/2012 | Fatta | |
| 2013/0218812 A1 * | 8/2013 | Weiss .................. | G06F 19/3418 |
| | | | 706/10 |
| 2016/0027278 A1 * | 1/2016 | McIntosh ........... | G08B 21/0423 |
| | | | 715/741 |
| 2016/0093197 A1 | 3/2016 | See | |
| 2016/0110523 A1 * | 4/2016 | Francois ................ | G06Q 50/24 |
| | | | 705/2 |

(Continued)

*Primary Examiner* — Toan N Pham

(57) ABSTRACT

A system is disclosed herein. The system includes a server, a software-application and a wearable-device. The system includes virtual groups to allows guardians or caretakers to identify/be alerted of any issues with a monitored subject. Events are triggered by various sensed parameters including heart rate, location, medication, etc. Notifications and alerts are sent through the software-application to the guardians and may be viewed by first responders via a First Response Portal. The system is useful for utilizing social grouping to enable family members or close friends to provide caregiver ability to a subject remotely.

21 Claims, 7 Drawing Sheets

(56) References Cited

U.S. PATENT DOCUMENTS

2016/0140828 A1* 5/2016 DeForest ............ G06F 19/3418
340/539.12
2016/0335879 A1* 11/2016 Carr ..................... G08B 25/006

* cited by examiner

PERSONAL MONITORING AND RESPONSE SYSTEM

CROSS REFERENCE TO RELATED APPLICATION

The present application is related to and claims priority to U.S. Provisional Patent Application No. 62/528,373 filed Jul. 3, 2017, which is incorporated by reference herein in its entirety.

BACKGROUND OF THE INVENTION

The following includes information that may be useful in understanding the present disclosure. It is not an admission that any of the information provided herein is prior art nor material to the presently described or claimed inventions, nor that any publication or document that is specifically or implicitly referenced is prior art.

1. Field of the Invention

The present invention relates generally to the field of monitoring systems and more specifically relates to a system for group monitoring of a subject.

2. Description of Related Art

Providing for the safety of individuals who live or travel alone while also safeguarding their privacy is challenging. Anyone needing medical attention, who is either incapacitated during the time of the event, or similarly, someone with mental disabilities, may not be able to make a request for help or provide necessary information to first response services in order to get appropriate treatment. Furthermore, the longer treatment is delayed, the more severe the injuries may get; and in some cases, the injuries may be irreversible. Thus, a suitable solution is desired.

U.S. Pub. No. 2012/0203076 to Jean Pierre Fatta relates to a portable physiological data monitoring device. The described portable physiological data monitoring device includes a housing, parameter sensing devices, a processing unit, and data communication units. The housing defines an inner surface for establishing physical contact with the patient's body part, and an outer surface opposing the inner surface. The parameter sensing devices acquire physiological data associated with the patient's physiological parameters. The processing unit processes the acquired physiological data and patient information. The data communication units, capable of synchronizing with responder devices, transmit the processed physiological data and the patient information to a base monitoring unit, a remote monitoring station, and/or responder devices via one or more transceivers and data communication interfaces for initiating relief measures.

BRIEF SUMMARY OF THE INVENTION

In view of the foregoing disadvantages inherent in the known monitoring systems art, the present disclosure provides a novel personal monitoring and response system. The general purpose of the present disclosure, which will be described subsequently in greater detail, is to provide a system for utilizing social grouping to enable family members or close friends to provide caregiver ability to a subject remotely.

A system is disclosed herein. The system includes a server which may include a server-processor and a server-memory having a server-database. The server-database may be configured to store at least one subject-profile file, at least one guardian-profile file, and at least one event-file. Further, a software-application may be provided that may be downloadable to an electronic-device and communicably coupled to the server.

An existing subject-device may be used with the system and may be communicably coupled to the server. The subject-device may include a controller, a display and a sensing-means configured to sense at least one preset health-parameter of the at least one subject. The controller may be configured to generate at least one health-signal and send the at least one health-signal to the server.

A method of using system is also disclosed herein. The method of using system may comprise the steps of: providing the system as above; creating a guardian-profile via the software-application; creating a subject-profile via the software-application; inputting subject-data to the subject-profile via the software application; syncing at least one subject-device of the at least one subject to the system; and monitoring the health of the at least one subject via the software-application.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, a personal monitoring and response system, constructed and operative according to the teachings of the present disclosure.

The various embodiments of the present invention will hereinafter be described in conjunction with the appended drawings, wherein like designations denote like elements.

DETAILED DESCRIPTION

Figure 1:
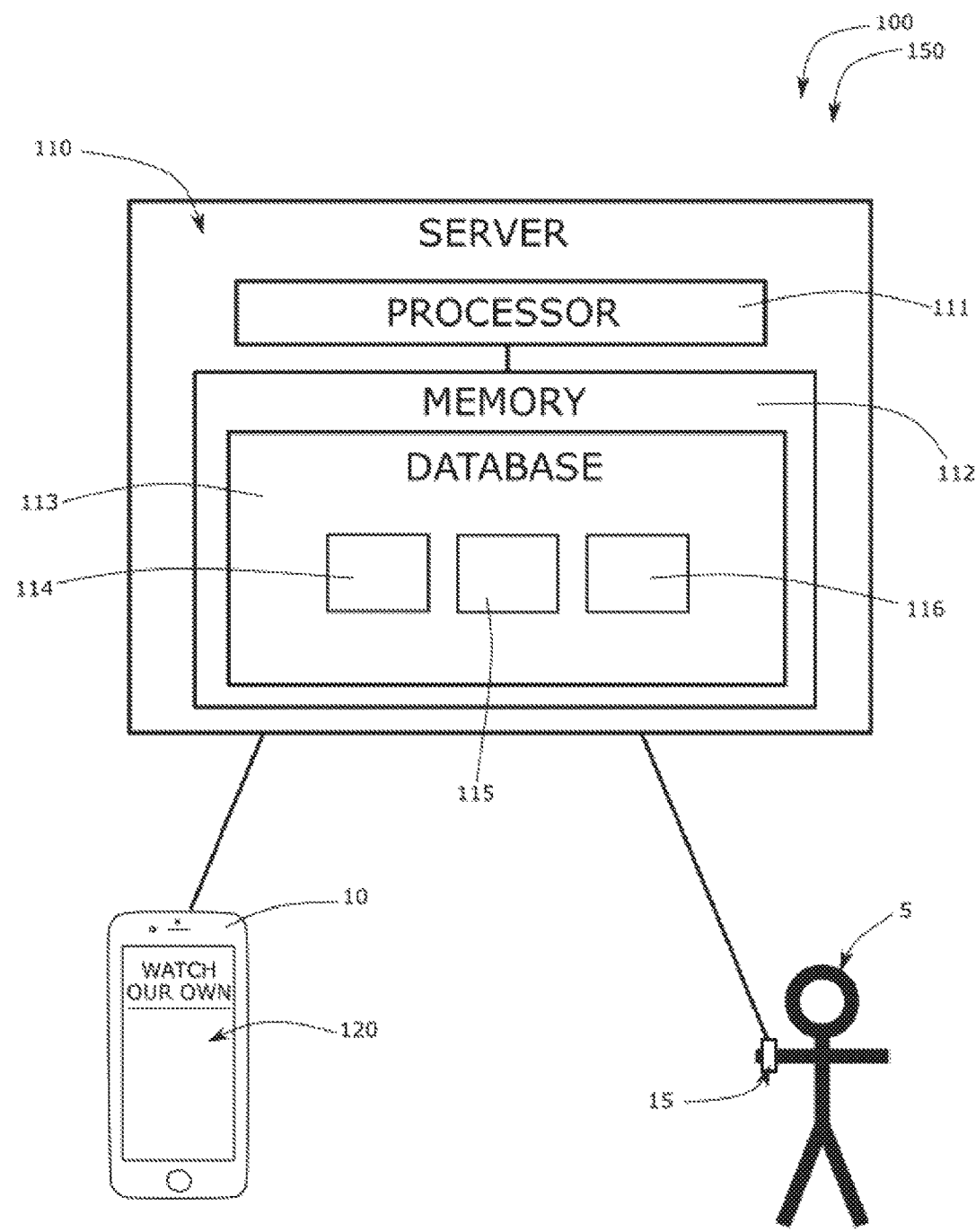
FIG. 1 is a front perspective view of the system during an 'in-use' condition, according to an embodiment of the disclosure.

As discussed above, embodiments of the present disclosure relate to monitoring systems and more particularly to a personal monitoring and response system as used to improve the system for group monitoring of a subject.

Generally, disclosed is a software and schedule program capable of keeping track of at-risk individuals. The program may be comprised of a virtual group system that allows guardians or caretakers to identify any issues with the monitored person. The virtual group system may be comprised of the at-risk individual's family or friends. Notifications and alerts may be sent through the application in order to identify injuries or suspicious interactions.

The system may include an "angel" member; a "guardian" member; an "admin" member; and a "caretaker/caregiver" member. The angel member may be the at-risk individual that is being watched over by the virtual group. The guardian may be a member that accepts responsibility to receive event notifications from the system regarding the angels they are watching over and leverage the application to provide help via first response or group participation. The admin member may be a member who is financially responsible for subscription to the system and may invite other members to join his/her group. Finally, the caretaker/caregiver member may be a member who is the legal guardian of the angel and is able to provide all information about the angel. This caretaker/caregiver member may have the ability to revoke any invite sent to members and revoke any existing relationships.

The system may be configured to store medical information about the angel. For example, the medical information may be prescriptions, allergies, medical conditions, vaccinations, etc. The prescription information may be private or public. In the private mode, the prescription may only be viewed by the angel; the caretaker; and a first responder. However, the first responder may only view the private mode once event access has been allowed via a First Responder Portal. In the public mode, the guardian may view the prescription information if an "Access Control List" (ACL) allows it. The ACL may allow the guardians to see the prescription information all of the time or during an event only.

Personal information of the angel may be inputted into the system. The personal information may include an address of the angel; pictures of the angel; will documentation; Do Not Resuscitate documentation and location of the documents in the home; location of electrical power shut off; location of boiler shut off; location of bedrooms in a house the angel member is residing; information regarding pets in the house; information regarding hazardous materials in the house; alternative power source shutoff; and emergency contacts. Examples of hazardous materials may be gun ammunition/reloading equipment. Examples of alternative power source shutoffs may be solar cell, thermal heating or windmill.

The system may further include schedules. Such schedules may include a date and time guardians are scheduled to watch the angel member(s). The guardians may not receive notifications if they are not scheduled to be on watch. This feature may be called an "Angel's Personal Guardian Scheduler". Further, the schedules may include a date and time medicines are to be administered with low/medium/high alert. The low alert may include no notifications sent if the angel member does not acknowledge the reminder. The medium alert may include the caretaker being sent an event notification if the angel member does not acknowledge the reminder; and the high alert may include all guardians being sent event notifications if the angel member fails to acknowledge the reminder. In addition to this, the schedules may include date/time location services. This may include geofencing to a pre-specified address the caregiver wants to ensure their angel member is during the time indicated on schedule. Failure may generate a location services event sent to all guardians to find the angel member. There may be a server-based polling/trigger to the care recipient's mobile device to acquire location of the angel 10-15 minutes before the scheduled time to show "breadcrumb" path in case of the location event.

As mentioned above, groups may be integral to the system. The groups may be made up of family and friends. A price of the subscription service may be based on membership rather than relationships within the group. Assembly of groups may include invite processes. For example, there may be an invite process with guardian to angel relationships and an invite process with caretaker to member. Further, the groups may consist of primary and secondary groups. Notifications may be active based on schedule or manual. Members with relationships with other subscribers in different groups may receive notifications during an event. In this embodiment, the members may only receive notifications based on status or when scheduled to be active. The primary group may always remain active.

As discussed briefly above, the system may include events. The event engine may be activated by heart rate (via a wearable device worn by the angel); location (by geofencing); prescription schedule; or self-activation. Notifications may be sent to the guardians/caretakers via push notification or via SMS regardless of the group. The notification may include location of the angel (or the last known location) and all guardians that have acknowledged the event. Further, event triggers and sub-event triggers may be displayed, and these events and sub-events may be logged for the admin/caretakers. The guardian in charge may be able to trigger first response access to the angel's information and this trigger may activate a motivation to the group. In addition to this, a chat engine, group call or video call feature may be integrated in the system to allow the members to communicate during the event. The video call may allow real time video stream to the first response portal. The system may save all of the chat information so that members are able to look back on the events history.

The system may include security features. For example, the caretaker/caregiver member must be the legal guardian or power of attorney of the angel to set up all of the angel's information on the system. Further security features may include the guardians being blocked or allowed visibility to angel member all the time or ONLY during an "event"; the First Response Portal being initiated by the guardian in charge of the event and the ability to revoke; the guardian in charge status having the ability to be transferred via request/approval process; the notification to guardian/admins of event changes (e.g., secondary event, escalation to First Response or 911); Images and documentation being secured via application session token and TLS to S3 site; and a password recovery process. The password recovery process may include enforcing strong password rules, providing 5 data items user can provide for verification purpose, pin to phone reset, etc. The system may also further include a recovery process whereby the caretaker/caregiver member has the ability to recover a change and reset to original settings.

Referring now more specifically to the drawings by numerals of reference, there is shown in FIGS. 1-7, various views of a system 100.

FIG. 1 shows a system 100 during an 'in-use' condition 150, according to an embodiment of the present disclosure. As illustrated, the system 100 may include a server 110, and a software-application 120. The system 100 may be configured for group monitoring of the health of at least one subject 5 (the angel member as above). The monitoring may be accomplished via an existing subject-device 15. As shown here, the at least one subject-device 15 may be a wearable-device. Further, the at least one subject-device 15 may be a mobile-device.

The server 110 may include a server-processor 111 and a server-memory 112. The server-memory 112 may have a server-database 113 configured to store at least one subject-profile file 114, at least one guardian-profile file 115, and at least one event-file 116. In a preferred embodiment, the guardian-profile file may correspond to the guardian member as mentioned above. In this embodiment, the server-database 113 may further include a caretaker information file corresponding to the caretaker/caregiver member as also mentioned above. The software-application 120 may be downloadable to an electronic-device 10 and communicably coupled to the server. As shown here, the electronic-device 10 may be a smartphone. However, it should be appreciated that any electronic-device 10 may be used. For example, desktop computers, tablet computers, laptop computers, etc.

Figure 2:
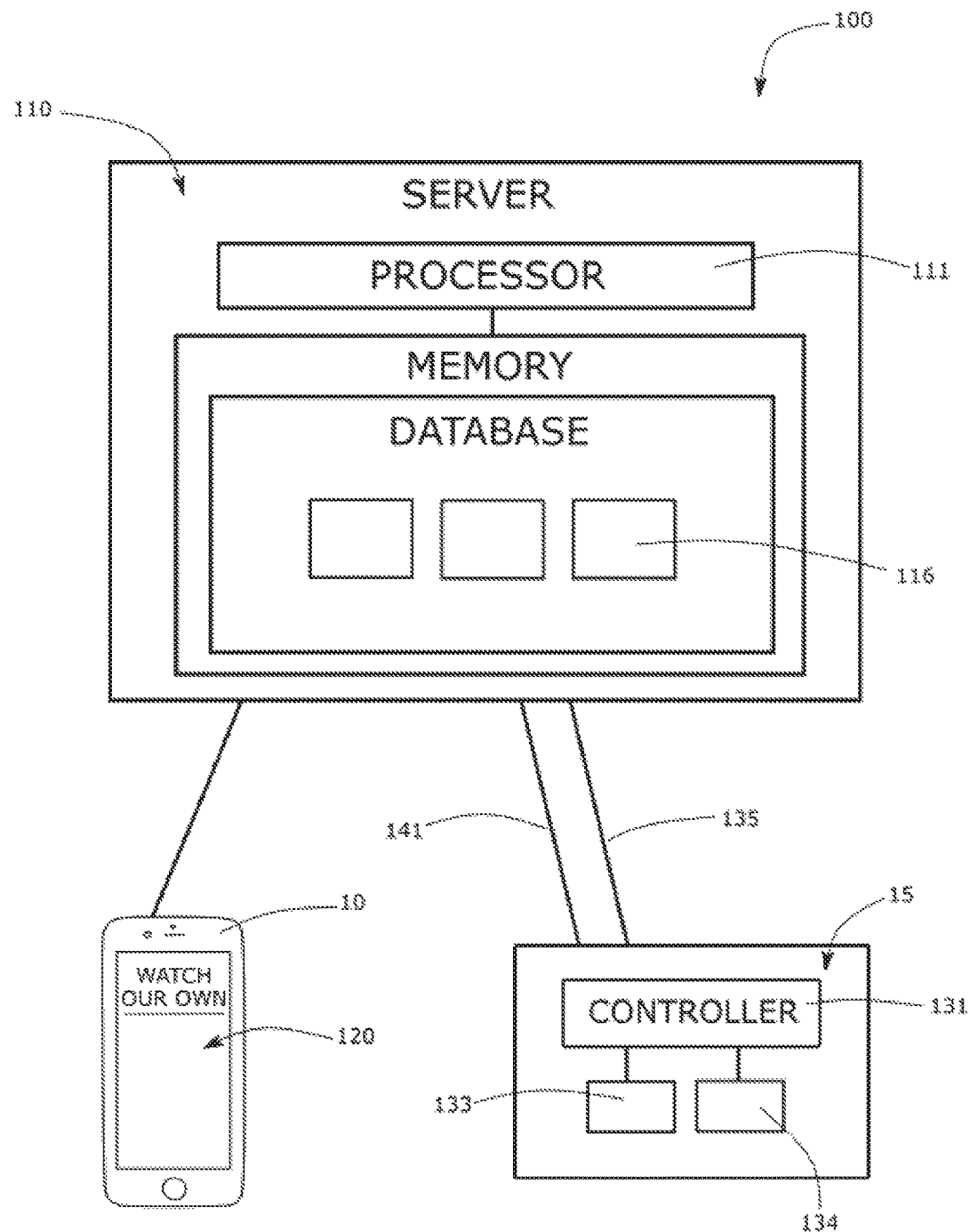
FIG. 2 is a front perspective view of the system of FIG. 1, according to an embodiment of the present disclosure.

FIG. 2 shows a front perspective view of the system 100 of FIG. 1, according to an embodiment of the present disclosure. As discussed above, the monitoring of the at least one subject 5 (FIG. 1) may be accomplished via at least one subject-device 15. The at least one subject-device 15, or a combination of subject-devices 15 may be communicably coupled to the server 110. Further, the at least one subject-device 15 or the combination of subject-device 15 may include a controller 131, and a sensing-means 133. In one embodiment, the at least one subject-device 15 may further include a location-sensing means 134.

The sensing-means 133 may be configured to sense at least one preset health-parameter of the at least one subject 5, and the controller 131 may be configured to generate at least one health-signal 141 and to send the at least one health-signal 141 to the server 110. The server-processor 111 may be configured to receive the at least one health-signal 141, retrieve a corresponding said at least one event-file 116, and send the at least one event-file 116 for display as a notification on the electronic-device 10. An event may then be created on the system 100 and as such, the guardian members and the angel member may then have access to view the event via the software-application 120. The retrieval of the at least one event-file 116 may be triggered by heart rate, location, prescription schedule or self-activation and may activate an event within the system. The at least one health-signal 141 may also be manually activated by the at least one subject 5 (FIG. 1) via the at least one subject-device 15. For example, if the at least one subject 5 (FIG. 1) feels threatened, is in a dangerous situation, or feeling unwell, the at least one subject 5 (FIG. 1) may trigger the at least one health-signal 141.

In one embodiment, the location-sensing means 134 may be configured to sense a location-parameter of the at least one subject 5 (FIG. 1). As discussed above, this may be via geofencing. In this embodiment, the location-sensing means 134 may be GPS, RFID, etc. As shown, the controller 131 may be configured to generate at least one location-signal 135 and send the at least one location-signal 135 to the server. The server-processor 111 may be configured to receive the at least one location-signal 135, retrieve another corresponding said at least one event-file 116, and send the corresponding said at least one event-file 116 for display as a notification on the electronic-device 10. As mentioned above, the location-signal 135 may be triggered if the location-sensing means 134 senses that the at least one subject 5 (FIG. 1) is not in a predetermined place at a predetermined time. The location sensing-means 133 may then send the location of the at least one subject 5 (FIG. 1) (or last known location of the at least one subject 5) as a notification to the group of guardian members watching over the at least one subject 5 (FIG. 1) at the time on the schedule.

In one embodiment, prior to creation of the event, the server-processor 111 may receive the at least one health-signal 141 or the at least one location-signal 135 and trigger a phone call to the at least one subject 5. A first phone call may be placed to a cell number of the at least one subject 5. If the at least one subject 5 fails to answer, a second phone call may be placed to a landline of the at least one subject 5. If both phone calls are not answered, the server-processor 111 retrieve the corresponding said at least one event-file 116, create the event for viewing, and send the corresponding said at least one event-file 116 for display as a notification on the electronic-device 10.

Figure 3:
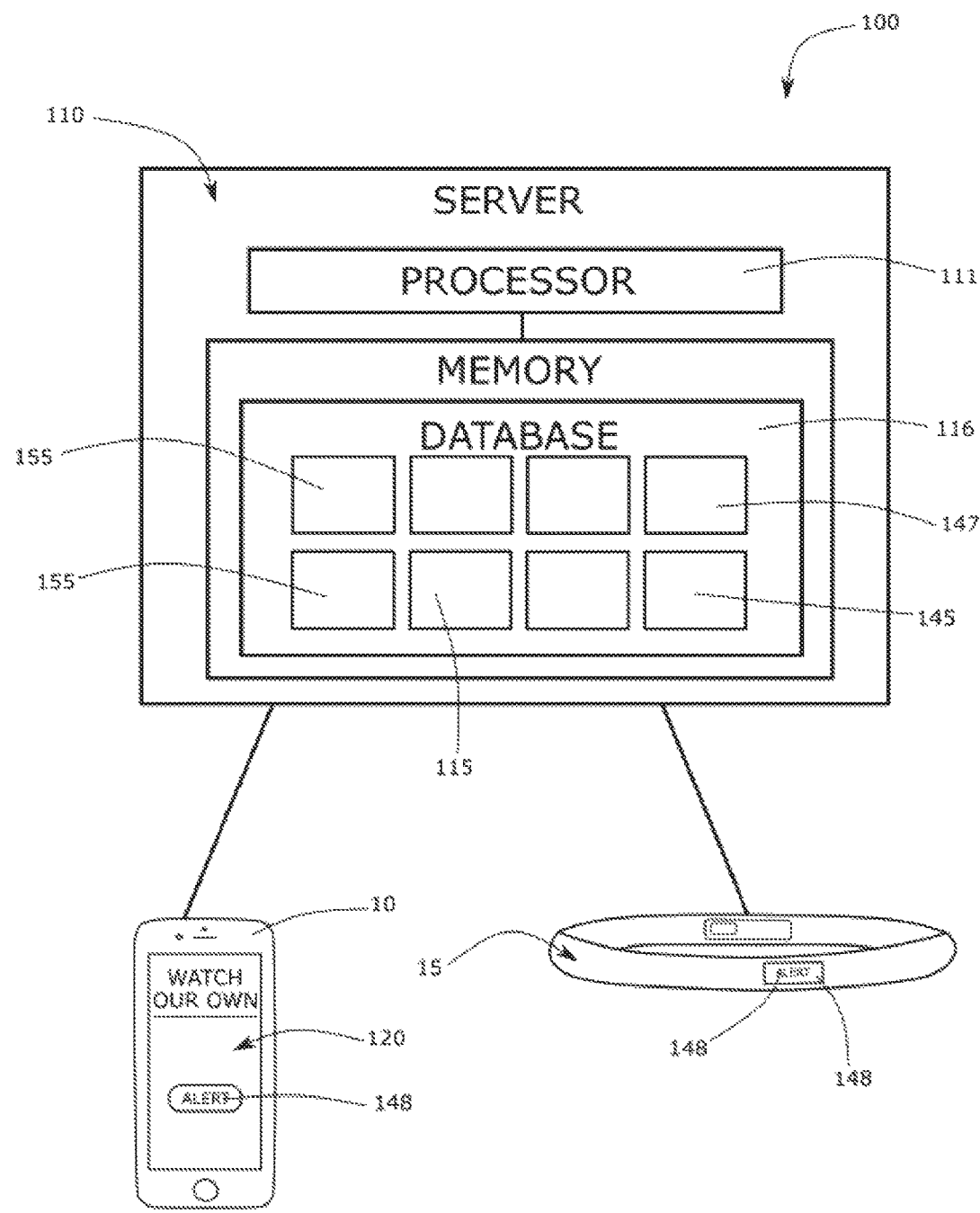
FIG. 3 is a front perspective view of the system of FIG. 1, according to an embodiment of the present disclosure.

FIG. 3 shows a front perspective view of the system 100 of FIG. 1, according to an embodiment of the present disclosure. Further, as has been discussed as an integral part of the system 100, the system 100 may be particularly useful for utilizing groups to monitor the at least one subject 5 (FIG. 1). As such, the server-database 113 may be configured to store at least one group-information file 155. The at least one group-information file 155 may include information such as members of the group, schedules of the group, invitations that have been sent to join a group, invitations that have been accepted, etc.

In one embodiment, the server-database 113 may be further configured to store at least one schedule-file 145. The at least one schedule-file 145 may include at least one duty-status file 146 corresponding to the at least one guardian-profile file 115. Particularly, the at least one schedule-file 145 may include information pertaining to the schedules within the group. In this embodiment and as discussed above, the at least one duty-file may detail when the at least one guardian is scheduled to receive notifications regarding an event.

In addition to this, the at least one schedule-file 145 may further include at least one medication-time file 147, and the server-processor 111 may be configured to generate at least one medication-alert 148 based on the at least one medication-time file 147. As discussed above, there may be different levels of alerts from low, medium to high. In one embodiment, the notification may be a push-notification. In another embodiment, the notification may be a text-message. Notifications to the at least one subject 5 may be sent to the at least one subject-device 15 (shown here to be a wearable-device). The notification may include information such as location of the at least one subject 5 or last known location of the at least one subject 5; event triggers or sub-event triggers, guardian members who have acknowledged the notification, etc.

Figure 4:
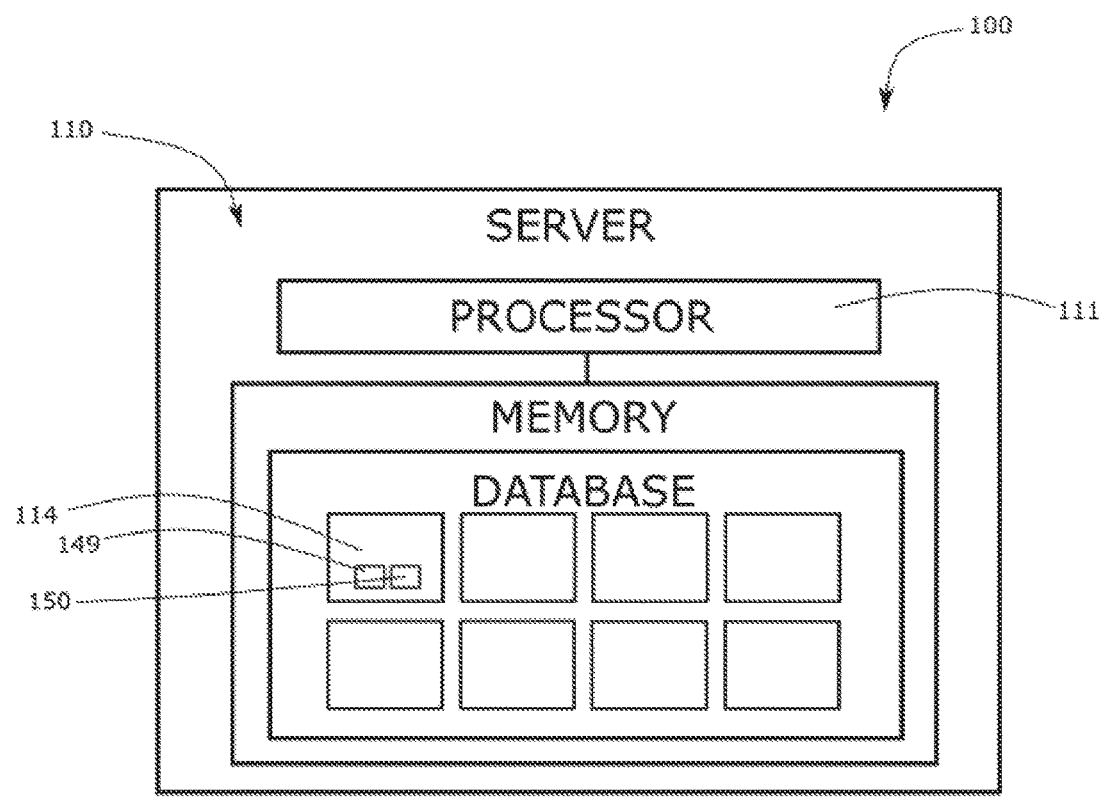
FIG. 4 is a front perspective view of the system of FIG. 1, according to an embodiment of the present disclosure.

FIG. 4 shows a front perspective view of the system 100 of FIG. 1, according to an embodiment of the present disclosure. As shown here and as discussed above, the at least one subject-profile file 114 may include at least one medical-information file 149 relating to the at least one subject 5. The at least one subject-profile file 114 may further include at least one personal-information file 150 relating to the at least one subject 5. Examples of medical-information file 149 contemplated may include prescriptions, allergies, medical conditions, vaccinations, etc. Further, examples of personal information files contemplated may include an address of the angel; pictures of the angel; will documentation; Do Not Resuscitate documentation and location of the documents in the home; location of electrical power shut off; location of boiler shut off; location of bedrooms in house; information regarding pets in the home; information regarding hazardous materials; alternative power source shutoff; and emergency contacts. When the event is triggered, a guardian member may provide access to the First Response Portal which may provide information relating to the at least one subject 5 such as personal information, medical information, location, trigger events to the first responder.

Figure 5:
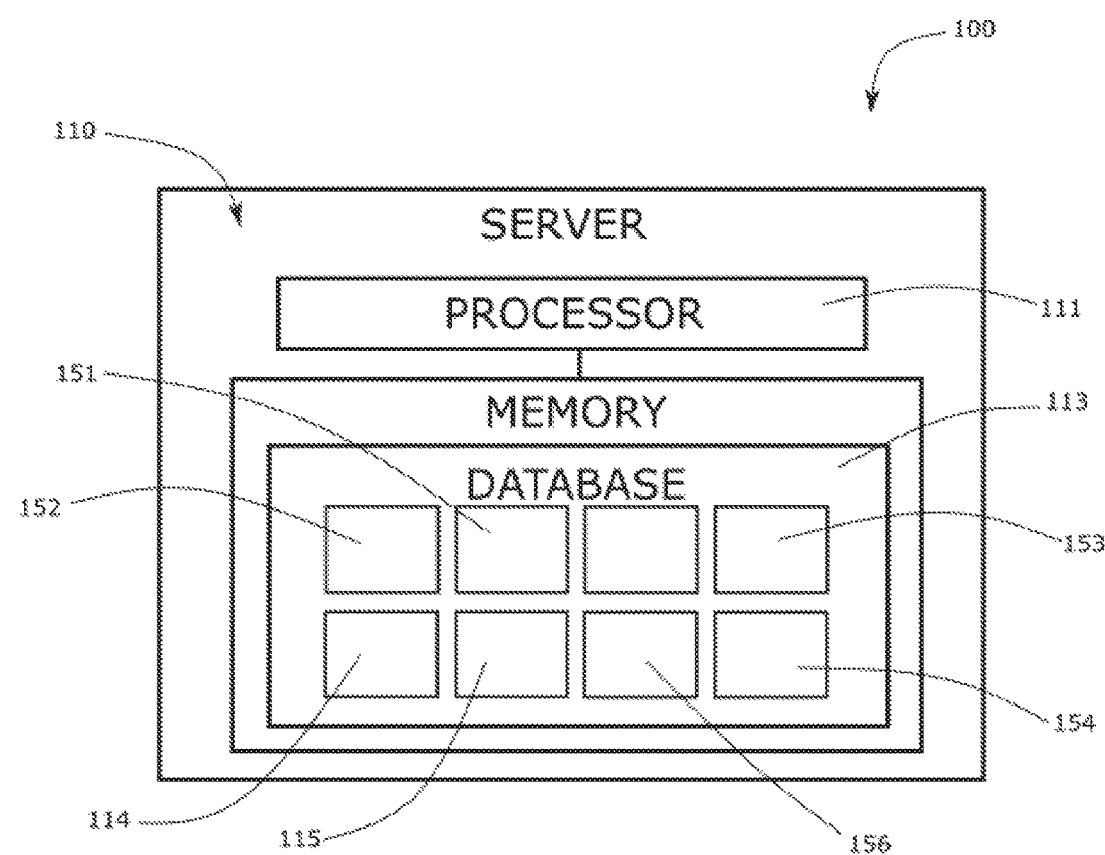
FIG. 5 is a front perspective view of the system of FIG. 1, according to an embodiment of the present disclosure.

FIG. 5 shows a front perspective view of the system 100 of FIG. 1, according to an embodiment of the present disclosure. The server-database 113 may be configured to store information pertaining to different profiles. The different profiles contemplated are the angel member, the guardian member, the administrative member and the caretaker/caregiver member. As such, the server-database 113 may further be configured to store at least one administrative-profile 151 and at least one caregiver-profile 152 along with the at least one subject-profile file 114 and the at least one guardian-profile file 115. In one embodiment, each profile may include log-in information and the server-database 113 may be configured to store at least one log-in information file 156.

The log-in information file 156 may include username and password such that when a member logs in to the software-application 120 the server-processor 111 is able to log in to the correct profile for the member. In addition to this, the server-database 113 may be further configured to store at least one security-information file 154. As discussed above, the security-information file 154 may include features such as the caretaker/caregiver member having to be legal guardian or power of attorney of the at least one subject 5; guardians being blocked from viewing the at least one subject 5 all of the time; ability to provide and revoke access to the First Response Portal; ability to revoke the guardian member in charge; the notifications; password recovery process, etc.

In one embodiment, the administrative member may sign up to the system 100 on a subscription basis. The subscription may be weekly, bi-weekly, monthly or yearly. In this embodiment, the server-database 113 may be configured to store at least one billing-information file 153. The billing-information file 153 may include direct deposit bank information such that the server-processor 111 is able to actuate payment at a predetermined time.

Figure 6:
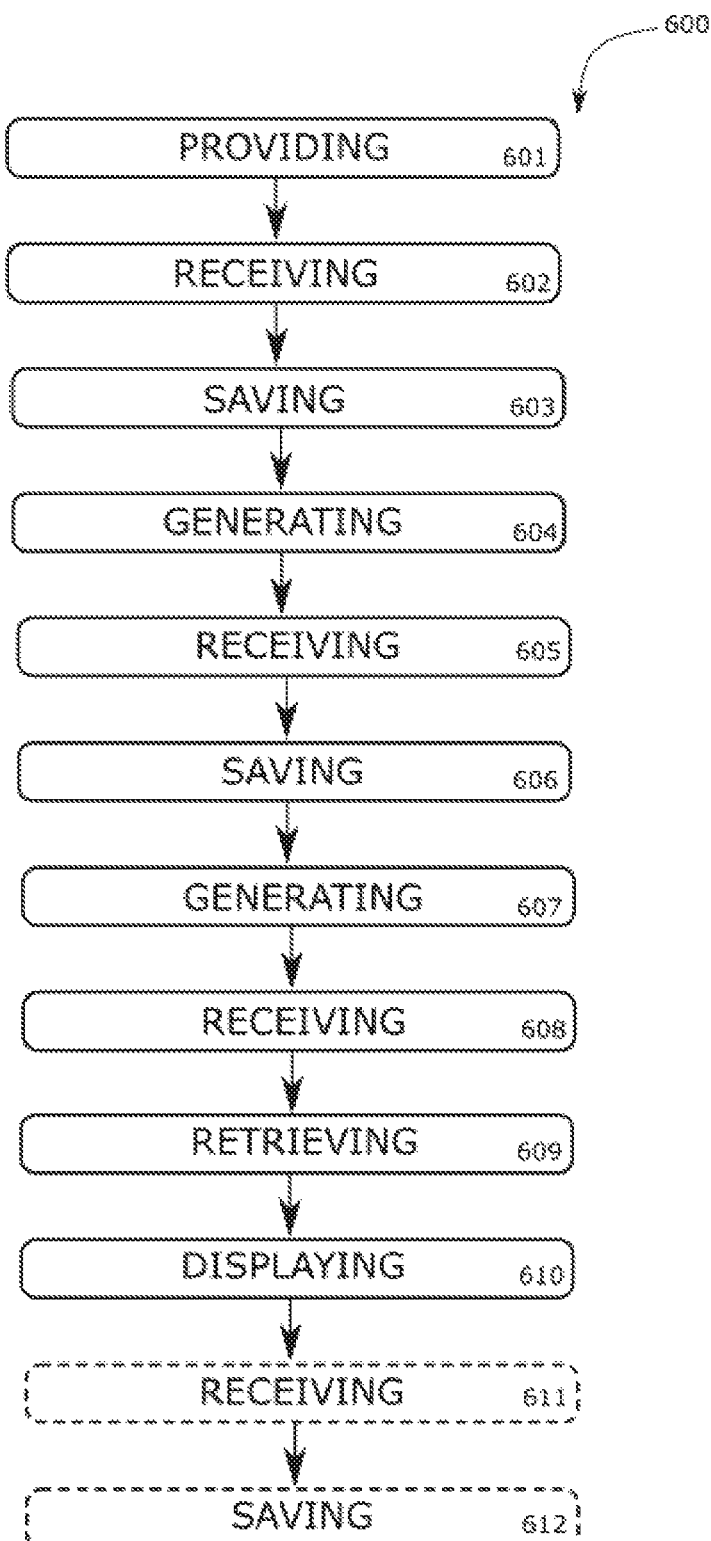
FIG. 6 is a flow diagram illustrating a method of providing the system, according to an embodiment of the present disclosure.

FIG. 6 is a flow diagram illustrating a method of providing a system for monitoring the health of at least one subject 600, according to an embodiment of the present disclosure. As illustrated, method of providing a system for monitoring the health of at least one subject 600 includes the steps of: step one 601, providing the system 100 as above; step two 602, receiving a first user-input at the server-processor 111 via the software application; step three 603, saving the first user-input as at least one guardian-profile file 115 on the server-database 113; step four 604, generating a guardian-profile on the software-application 120; step five 605, receiving a second user-input at the server-processor 111 via the software-application 120; step six 606, saving the second user-input as at least one subject 5-profile file 114 on the server-database 113; step seven 607, generating a subject-profile on the software-application 120; step eight 608, receiving at least one of a health-signal 141 and a location-signal 135 at the server-processor 111 via the at least one subject-device 15; step nine 609, retrieving at least one corresponding event-file from the server-database 113; and step ten 610, displaying the at least one corresponding event-file as a notification on at least one of the software-application 120 and the at least one subject-device 15.

Further steps may include: step eleven 611, receiving a third user-input at the server-processor 111 via the software application; and step twelve 612, saving the third user-input as at least one billing-information file 153 on the server-database 113.

Figure 7:
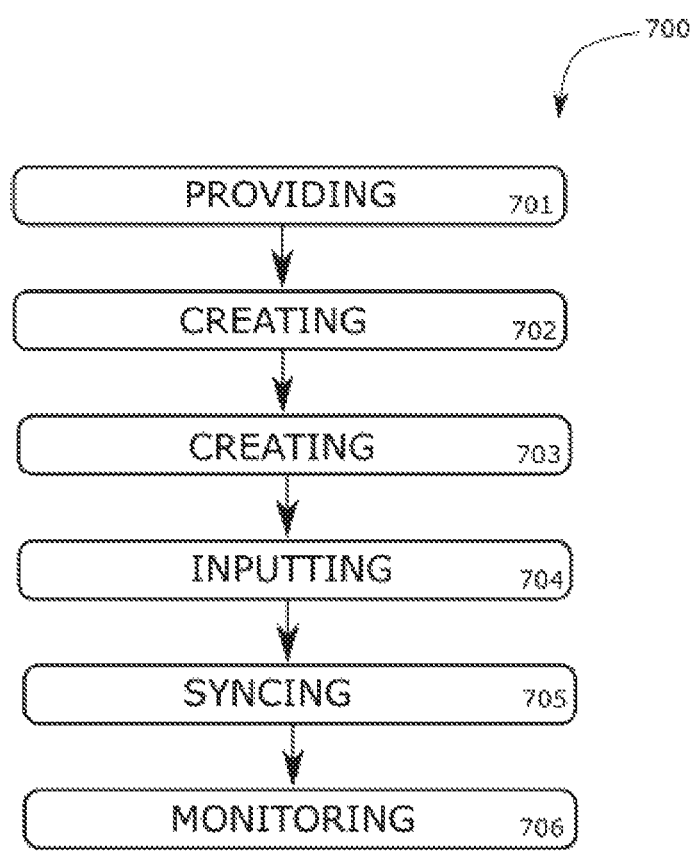
FIG. 7 is a flow diagram illustrating a method of use for system, according to an embodiment of the present disclosure.

FIG. 7 is a flow diagram illustrating a method of using a system for monitoring the health of at least one subject 700, according to an embodiment of the present disclosure. As illustrated, the method of using a system for monitoring the health of at least one subject 700 may include the steps of: step one 701, providing the system 100 as above; step two 702, creating a guardian-profile via the software-application 120; step three 703, creating a subject-profile via the software-application 120; step four 704, inputting subject-data to the subject-profile via the software application; step five 705, syncing the at least one subject-device 15 of the at least one subject 5 to the system 100; and step six 706, monitoring the health of the at least one subject 5 via the software-application 120. The system 100 may further create reports based on the events for view by the caregiver member as above.

It should be noted that step eleven 611 and step twelve 612 are optional steps and may not be implemented in all cases. Optional steps of method of use 600 are illustrated using dotted lines in FIG. 6 so as to distinguish them from the other steps of method of use 600. It should also be noted that the steps described in the method of use can be carried out in many different orders according to user preference. The use of "step of" should not be interpreted as "step for", in the claims herein and is not intended to invoke the provisions of 35 U.S.C. § 112(f). It should also be noted that, under appropriate circumstances, considering such issues as design preference, user preferences, marketing preferences, cost, structural requirements, available materials, technological advances, etc., other methods for system 100 (e.g., different step orders within above-mentioned list, elimination or addition of certain steps, including or excluding certain maintenance steps, etc.), are taught herein.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A system for monitoring the health of at least one subject, the system comprising:

a server including a server-processor and a server-memory, the server-memory having a server-database, and wherein the server-database is configured to store at least one subject-profile file, at least one guardian-profile file, and at least one event-file; and a software-application downloadable to an electronic-device, the software-application communicably coupled to the server; and at least one subject-device containing the software application configured to monitor a subject, detect a predetermined triggering event, and transmit a signal upon detection of the predetermined triggering event; and wherein the server-processor is configured to receive at least one health—the signal from the at least one subject-device, retrieve a corresponding said at least one event-file, and send the at least one event-file for display as a notification on the electronic-device.

2. The system of claim 1, wherein the server-database is further configured to store at least one schedule-file.

3. The system of claim 2, wherein the at least one schedule-file includes at least one duty-status file, and wherein the at least one duty-status file corresponds to the at least one guardian-profile file.

4. The system of claim 3, wherein the at least one schedule-file further includes at least one medication-time file, and wherein the server-processor is configured to generate at least one medication-alert based on the at least one medication-time file.

5. The system of claim 1, wherein the at least one subject-device is a wearable-device configured for attachment to the at least one subject and communicably coupled to the server, the wearable-device including a controller, a display and a sensing-means, the sensing-means configured to sense at least one health-parameter of the at least one subject, and wherein the controller is configured to generate at least one health-signal upon detection by the sensing means of at least one predetermined triggering health parameter, and further configured to send the at least one health-signal to the server.

6. The system of claim 1, wherein the detection by the sensing means of at least one predetermined triggering event comprises detection of a failure by the at least one subject to acknowledge a medication reminder, or detection of a predetermined heart rate.

7. The system of claim 1, wherein the at least one subject-device further includes a location-sensing means configured to sense a location-parameter of the at least one subject, and wherein the controller is configured to generate at least one location-signal upon sensing by the location-sensing means of a predetermined triggering location-parameter, and send the at least one location-signal to the server, and wherein the server-processor is configured to receive the at least one location-signal, retrieve another corresponding said at least one event-file, and send the corresponding said at least one event-file for display as a notification on the electronic-device.

8. The system of claim 7, wherein the sensing by the location-sensing means of a predetermined triggering location parameter comprises the location sensing means sensing that the at least one subject is not in a predetermined place at a predetermined time.

9. The system of claim 1, wherein the at least one subject-profile file includes at least one personal-information file relating to the at least one subject, and at least one medical-information file relating to the at least one subject.

10. The system of claim 1, wherein the server-database is further configured to store at least one administrative-profile file.

11. The system of claim 10, wherein the server-database is further configured to store at least one caregiver-profile.

12. The system of claim 11, wherein the server-database is further configured to store at least one billing-information file.

13. The system of claim 12, wherein the server-database is further configured to store at least one security-information file.

14. The system of claim 13, wherein the server-database is further configured to store at least one group-information file.

15. The system of claim 1, wherein the notification is a push-notification.

16. The system of claim 1, wherein
the server memory additionally has an application providing server-side chat engine, group call, or video call functionality,
and
the software-application has client-side chat engine, group call, or video call functionality.

17. A method of providing a system for monitoring the health of at least one subject, the method comprising:
providing the system for monitoring the health of at least one subject, the system including:
a server including a server-processor and a server-memory, the server-memory having a server-database, and wherein the server-database is configured to store at least one subject-profile file, at least one guardian-profile file, and at least one event-file; and
a software-application downloadable to an electronic-device, the software-application communicably coupled to the server; and
receiving a first user-input at the server-processor via the software application;
saving the first user-input as at least one guardian-profile file on the server-database;
generating a guardian-profile on the software-application;
receiving a second user-input at the server-processor via the software-application;
saving the second user-input as at least one subject-profile file on the server-database;
generating a subject-profile on the software-application;
receiving at least one of a health-signal and a location-signal at the server-processor via at least one subject-device, wherein the at least one subject-device is configured to monitor a subject, and transmit the at least one of a health-signal and a location-signal to the server-processor upon detecting a predetermined triggering subject health or location condition;
retrieving at least one corresponding event-file from the server-database; and
displaying the at least one corresponding event-file as a notification on at least one of the software-application and the at least one subject-device.

18. The method of claim 17, further comprising the steps of:
receiving a third user-input at the server-processor via the software application; and
saving the third user-input as at least one billing-information file on the server-database.

19. The method of claim 17, wherein detecting a predetermined triggering subject health or location condition by the at least one subject device comprises detecting a failure by the at least one subject to acknowledge a medication reminder, detecting a predetermined subject heart rate, or sensing that the at least one subject is not in a predetermined place at a predetermined time.

20. A system for monitoring the health of at least one subject, the system comprising:
- a server including a server-processor and a server-memory, the server-memory having server-side chat engine, group call or video call software and a server-database, and wherein the server-database is configured to store at least one subject-profile file, at least one guardian-profile file, and at least one schedule file;
- a software-application downloadable to an electronic-device, the software-application communicably coupled to the server and including client-side server-side chat engine, group call or video call software; and
- a subject-device containing the software-application configured to provide at least one reminder to the at least one subject, and to transmit an alert signal in accordance with a pre-defined alert level in the schedule file upon failure of the at least one subject to acknowledge the reminder.

21. The system for monitoring the health of at least one subject of claim 20, wherein the pre-defined alert level comprises at least two alert levels, and wherein an event notification is sent to at least one guardian when a failure of the at least one subject to acknowledge the reminder occurs at a higher one of the two alert levels.

* * * * *